United States Patent
Gotte et al.

(10) Patent No.: US 8,939,994 B2
(45) Date of Patent: Jan. 27, 2015

(54) SUCTION FIXING DEVICE

(75) Inventors: Hubert Gotte, Munich (DE); Jens Krugmann, Munich (DE)

(73) Assignee: Brainlab AG, Feldkirchen (DE)

( * ) Notice: Subject to any disclaimer, the term of this patent is extended or adjusted under 35 U.S.C. 154(b) by 1097 days.

(21) Appl. No.: 11/554,337

(22) Filed: Oct. 30, 2006

(65) Prior Publication Data

US 2007/0123774 A1    May 31, 2007

Related U.S. Application Data

(60) Provisional application No. 60/754,262, filed on Dec. 28, 2005.

(30) Foreign Application Priority Data

Oct. 28, 2005   (EP) ................... 05023728

(51) Int. Cl.
*A61B 19/00* (2006.01)
*A61B 17/00* (2006.01)
*A61B 17/30* (2006.01)

(52) U.S. Cl.
CPC ........... *A61B 17/00234* (2013.01); *A61B 19/26* (2013.01); *A61B 19/5244* (2013.01); *A61B 2017/306* (2013.01); *A61B 2017/308* (2013.01); *A61B 2019/5416* (2013.01); *A61B 2019/5483* (2013.01); *A61B 2019/5487* (2013.01)
USPC ........................................... 606/130; 606/97

(58) Field of Classification Search
USPC .............. 248/205.5–205.9, 206.1–206.4, 248/362–363; 294/64.1–64.3, 65; 451/494; 600/387, 414, 426, 37; 606/53, 130, 606/123, 204; 604/315–316
See application file for complete search history.

(56) References Cited

U.S. PATENT DOCUMENTS

| | | | | | |
|---|---|---|---|---|---|
| 2,146,859 | A | * | 2/1939 | Seklehner | 248/467 |
| 2,657,893 | A | * | 11/1953 | Puckert | 248/205.8 |
| 3,020,017 | A | * | 2/1962 | Watson | 248/205.8 |
| 3,536,149 | A | * | 10/1970 | Laird | 175/209 |
| 3,654,047 | A | * | 4/1972 | Berkowitz | 428/179 |
| 3,955,563 | A | * | 5/1976 | Maione | 601/106 |
| 4,291,866 | A | * | 9/1981 | Petersen | 269/1 |
| 4,369,793 | A | * | 1/1983 | Staver et al. | 600/387 |
| 4,814,185 | A | * | 3/1989 | Jones | 425/12 |
| 5,653,561 | A | * | 8/1997 | May | 408/67 |
| 5,662,677 | A | * | 9/1997 | Wimmer | 606/201 |
| 5,752,962 | A | * | 5/1998 | D'Urso | 606/130 |
| 5,897,882 | A | * | 4/1999 | Gonzalez et al. | 425/12 |
| 6,327,491 | B1 | * | 12/2001 | Franklin et al. | 600/429 |
| 6,338,619 | B1 | * | 1/2002 | Rusch | 425/11 |
| 6,345,192 | B1 | * | 2/2002 | Feucht et al. | 600/387 |

(Continued)

FOREIGN PATENT DOCUMENTS

| | | | |
|---|---|---|---|
| EP | 0 797 958 A1 | | 10/1997 |
| EP | 1 371 340 A1 | | 12/2003 |
| WO | WO 9306873 A1 | * | 4/1993 |

*Primary Examiner* — David Bates
*Assistant Examiner* — Samuel Hanna
(74) *Attorney, Agent, or Firm* — Tucker Ellis LLP

(57) ABSTRACT

A suction fixing device to be fixed to an organic base includes at least one low-pressure casing, at least one attachment device operative to apply a low pressure to the surface of said organic base; and a holding device operative to secure the fixing device to the organic base. The holding device engages the organic base when low pressure is applied to the surface of the organic base.

22 Claims, 1 Drawing Sheet

(56) References Cited

U.S. PATENT DOCUMENTS

| | | | |
|---|---|---|---|
| 6,478,271 B1* | 11/2002 | Mulholland | 248/205.8 |
| 6,595,999 B2* | 7/2003 | Marchione et al. | 606/96 |
| 6,656,109 B2 | 12/2003 | DeVries et al. | |
| 6,827,344 B1* | 12/2004 | Ristau | 269/21 |
| 7,179,224 B2* | 2/2007 | Willis | 600/205 |
| 7,338,020 B2* | 3/2008 | Magid | 248/206.2 |
| 2001/0029956 A1* | 10/2001 | Argenta et al. | 128/897 |
| 2002/0049369 A1 | 4/2002 | Spence et al. | |
| 2004/0092985 A1* | 5/2004 | Parihar et al. | 606/167 |
| 2004/0127908 A1* | 7/2004 | Roman et al. | 606/72 |
| 2004/0176659 A1* | 9/2004 | Peng et al. | 600/37 |
| 2005/0033322 A1 | 2/2005 | Lau et al. | |
| 2005/0075632 A1* | 4/2005 | Russell et al. | 606/53 |
| 2005/0119639 A1* | 6/2005 | McCombs et al. | 606/1 |
| 2007/0123774 A1 | 5/2007 | Gotte et al. | |
| 2007/0218101 A1 | 9/2007 | Johnson et al. | |

* cited by examiner

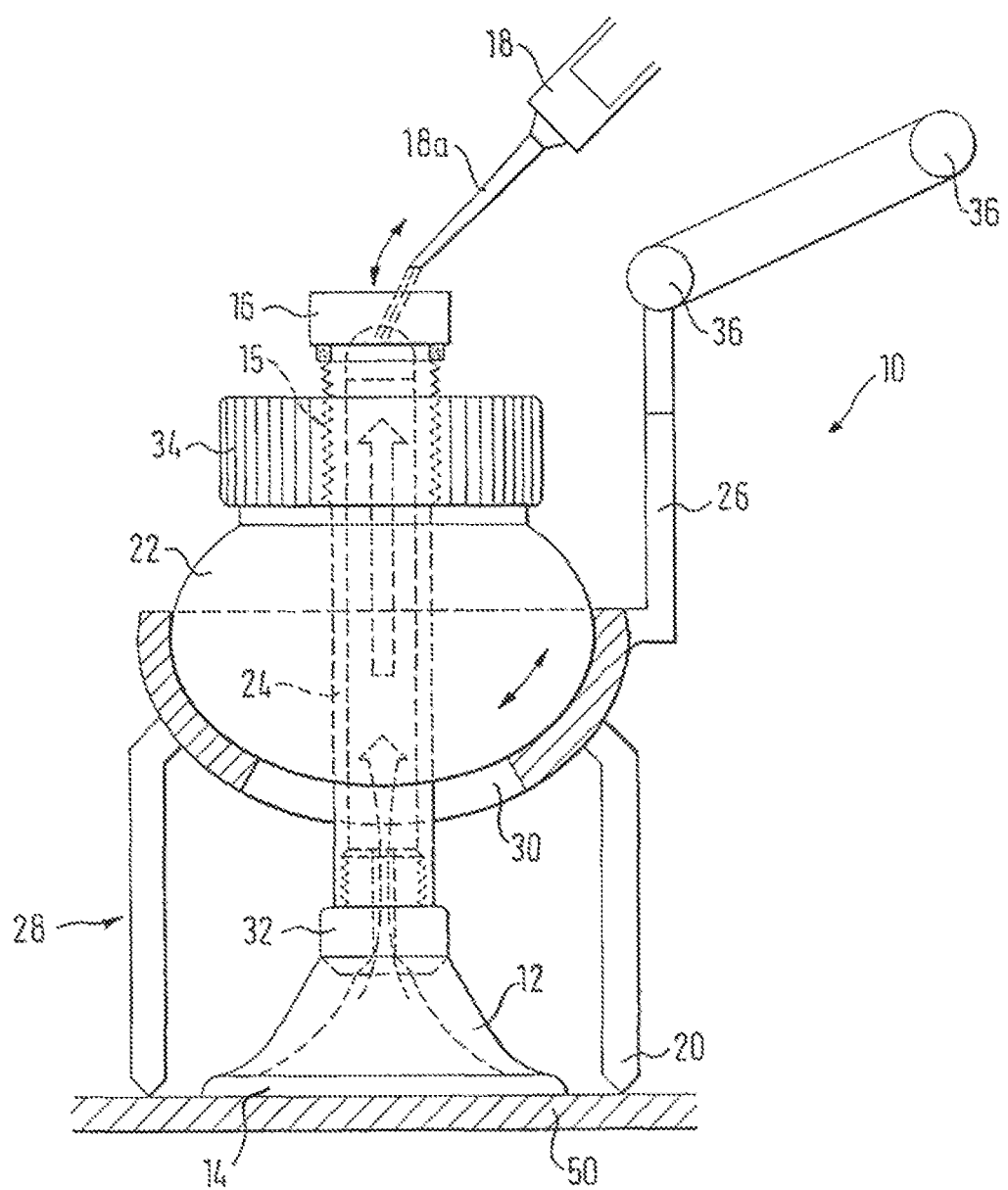

SUCTION FIXING DEVICE

RELATED APPLICATION DATA

This application claims priority of U.S. Provisional Application No. 60/754,262 filed on Dec. 28, 2005, which is incorporated herein by reference in its entirety.

FIELD OF THE INVENTION

The present invention relates to a suction fixing device to be fixed on an organic base, such as a bone structure. Furthermore, the invention relates to a method for fixing the suction fixing device and, more particularly, to fixing a reference or marker element to a bone structure.

BACKGROUND OF THE INVENTION

In recent years, surgical operation techniques have developed towards minimally invasive operating methods. These methods are often based on image-guided or computer-aided surgery. Such surgical methods typically utilize a marker, reference elements or array to high enable accuracy navigation during medical procedures, such as surgical operations, for example.

During a surgical operation, the reference or marker elements, once calibrated, are not disturbed or otherwise moved, since accuracy is closely related to maintaining orientation (and thus maintaining calibration) in the surgical operating space. Therefore, the marker, reference elements or array are rigidly and reliably fixed. The reference, marker elements or array may be fixed to an organic base, such as a bone structure for example, and therefore should be easily detachable from the organic base with a minimally invasive influence thereon.

Conventionally, screws or nails are commonly used to attach the marker, reference elements or arrays to the bone structure, wherein the bone is penetrated by these surgical tools. Accordingly, the screws or nails may injure the bone structure, which may weaken it, particularly if the bone has been spelled (as is possible in elderly patients), partially destroyed, or the like.

SUMMARY OF THE INVENTION

The present invention provides a fixing device that enables medical devices, such as surgical tools, reference arrays, or the like, to be attached and detached very quickly to/from an organic base, such as a bone or bone structure. The fixing device can be used as a surgical tool that allows a small area of contact, in particular on a bone structure, to be used for securely fixing to the bone structure. Moreover, the present invention provides a fixing device and/or surgical tool that does not need to penetrate into the organic base in order to be securely fixed to the organic base.

According to one aspect of the invention, a suction fixing device comprises at least one low-pressure casing, and at least one attachment device for applying a low pressure to the surface of said organic base.

A method of attaching the fixing device can include preparing and/or bringing an organic base into contact with the attachment device and/or a holding device. Once contact has been made, a low pressure can be generated in a low-pressure casing, and the device can be fixed to the organic base, such as a bone, by means of a low-pressure atmosphere in the low-pressure casing, thereby attaching the marker, reference elements or array at a certain position.

The fixing device can further include at least one valve means for connecting an evacuation device and/or at least one integrated evacuation device, the evacuation device generating a low pressure in said low-pressure casing.

Using the suction fixing device, it is possible to quickly attach and detach the device to/from a small area in the surgical field, e.g., the organic base, by creating a low pressure in the low-pressure casing. The attachment device of the suction fixing device can be attached to a bone structure, and low pressure or a vacuum can be generated and maintained in the low-pressure casing. With low pressure or vacuum in the low-pressure casing, atmospheric pressure presses the suction fixing device against the organic base. The device can thus be securely fixed using a simple surgical tool, such that the marker, reference element or array is securely fixed to the suction fixing device.

The valve means can be used to connect an evacuation device to the suction fixing device in order to generate low pressure in the low-pressure casing. A syringe, for instance, can be used to lower the pressure in the low-pressure casing. Another way of generating a low pressure is to use an integrated evacuation device, e.g., the evacuation device, for instance a suction piston, syringe or the like, can be part of the suction fixing device. For example, the evacuation device can be directly connected to the low-pressure casing. In this case, it is preferable that a piston rod of the evacuation device be lockable or blockable, to avoid atmospheric pressure pressing the piston rod into the piston volume, thereby releasing the low pressure in the piston volume. It is also possible to connect an electrical valve pump to the valve means, wherein said valve pump can be disconnected once the low pressure has been generated in the low-pressure casing. To detach the suction fixing device, the valve means can be opened or the syringe can be released so as to equalize the low pressure in the low-pressure casing.

It is also possible that the edge of the suction fixing device be bent or otherwise shaped to adjust the suction fixing device to more complicated surfaces of a bone or a joint.

A holding structure can be formed close to said attachment device. This holding structure can be adjusted so as to be effective in the plane of the attachment device used to apply the low pressure to the surface of the organic base. Accordingly, if the fixing device, for instance a suction cup, is urged against the organic base (e.g., "bone structure"), the holding structure can be urged against the surface of the bone structure and can secure the suction fixing device against shifting forces and/or torques applied to it. Accordingly, the holding structure can have a structure such as a spiked or ridged structure, wherein said spikes or ridges or the like are urged against the surface of the bone structure when generating the low pressure in the low-pressure casing, which in turn urges the suction fixing device according to the invention against the surface of the bone structure.

It is also possible to compensate a tilt angle between the suction cup on the holding structure for instance by means of elongating or shortening the holding structure on one or several sides thereof. For example, in case the holding structure includes some pin-shaped legs, in particular three pin-shaped legs, it is possible to elongate or shorten at least one of the legs to adjust the plane stretched by the ends of the legs to the plane of the suction cup.

A joint element can be provided for adjustably fixing surgical equipment to the suction fixing device. A marker, reference element or array, for example, can be fixed to the joint element. Such a marker, reference element or array can be used in image-guided surgical methods or computer-aided surgical methods, e.g., in connection with Vector Vision/ Trauma 2.5, both products of the assignee of the present application.

Further, a flexible connection can be interposed between the attachment device (e.g., the suction cup) and the evacuation device and/or the valve means. If the suction fixing device is slightly inclined while being fixed to the surface of the bone structure, it is possible for internal stresses, internal torques and the like to be exerted on the suction fixing device. This additional strain could loosen or contribute to loosening the suction fixing device. However, the flexible connection can be used to equalize such inclinations, stresses, torques or the like.

A frame can be provided that supports at least some of the parts of the suction device. The frame can support the low-pressure casing, the attachment device, the valve means or syringe, the evacuation device and so on, such that mechanical stability and, thus, the ability to securely fix the suction fixing device to the bone structure can be improved. Furthermore, the holding device can be formed at the end of the frame, such that the holding device is directed towards the surface of the bone structure.

Additionally, a joint element can be provided to absorb further strains/stresses, inclinations or torques and shifting forces such that a part of the suction fixing device can be pivoted or rotated. The function of the joint element can be assisted by the holding structure and vice versa.

To enable multiple degrees of freedom, the frame can be provided with at least one recess for guiding or routing the connection or flexible connection (which is preferably part of the low-pressure volume associated with the low-pressure casing). The recess can have larger dimensions than the connection or flexible connection, to allow additional degrees of freedom, in particular for movements by the joint element such as a ball joint.

Using the fixing device, it is possible to use a femoral marker array to pivot a hip center point. It is also possible, for instance, to use the device to attach and use a reference array when acquiring surface points, for example, in a gap of a joint in a human or animal body. The suction fixing device can be used to serve these purposes by attaching the device to a cartilage surface of the joint end of the femur, after opening a knee joint. Accordingly, the suction fixing device can be used in connection with most hip and knee applications, at least where computer-aided surgical techniques are used.

In summary, the invention can include a suction cup and a marker array mounted to the suction cup. The suction cup can be provided with a vacuum source such as an electrical vacuum pump or a mechanical suction device such as a syringe. The vacuum source can also be incorporated into the device. A piston rod, for example, can be formed as a screw which, if rotated, can pull the piston out of the evacuation device and create a vacuum that removes air or gas from the suction cup. While in most cases, it may be sufficient to simply use the suction cup as the low-pressure casing in connection with the attachment device, in some cases in which it is complicated to fix the suction fixing device by means of only the force exerted by atmospheric pressure, a holding device with pins, spikes, friction ridges or the like can also be used. The suction cup can be partially or completely made of silicone, rubber or the like. In addition, it is possible for the suction cup to be made of metal or glass and for only a suction lip provided on the cup to be made of silicone, rubber or the like. It is also possible to use more the one suction cup, e.g., two or three suction cups, wherein the other suction cup or cups are contacting the bone or joint structure at other locations, for instance at a rotationally shifted and/or linearly shifted position with respect to the first suction cup.

The present invention provides a fixing device that enables a surgical tool, marker array, etc. to be fixed to the bone structure without using penetrating surgical tools. Thus, the bone structure is not injured and the bone surface need not be penetrated.

BRIEF DESCRIPTION OF THE DRAWINGS

The forgoing and other embodiments of the invention are hereinafter discussed with reference to the drawings.

FIG. 1 illustrates an exemplary fixing device in accordance with the invention.

DETAILED DESCRIPTION

A preferred embodiment will now be described with reference to the FIG. 1. A fixing device 10 includes a low-pressure casing 12 which, for example, can be a suction cup. The low-pressure casing 12 can include an attachment device 14 which is operative to be brought into contact with an organic base 50, in particular a surface of a bone structure 50. The attachment device 14 can for instance include a flexible lip made of rubber, silicone or the like, to be attached to the bone surface 50 such that a low-pressure atmosphere in the low-pressure casing 12 can be maintained and is not released through a gap between a surface of the bone 50 and the attachment device 14.

An edge of the attachment device 14 with the corresponding lip also can have a bent shape. The low-pressure casing 12 can be connected to a valve means or adapter means 16. This valve or adapter means can be used to connect an evacuation device 18, such as, for example, a syringe 18 or an electrical vacuum pump (not shown), to the low-pressure casing 12. If a syringe 18 is used, the syringe can have a suction extension 18a couplable to the valve means or adapter means 16. If the syringe 18 remains connected to the adapter means 16, a piston rod (not shown) of the syringe 18 preferably is held in a fixed position, e.g., locked in a low-pressure position such that the low-pressure atmosphere in the low-pressure casing 12 can be maintained over a long period of time (e.g. for at least a period of time to perform the surgical procedure).

The low-pressure casing 12 can be connected by a connecting device 32 to a connection 24, which can be a flexible connection. The connection 24 can be connected and sealed to the valve or adapter means 16. A joint element 22, such as a ball joint, for example, may be provided to allow inclinations between the low-pressure casing 12 (and thus the attachment device 14) and a coupling element 26. The coupling element 26 can support one or more marker or reference elements 36, which together can form a marker array. A frame 28 can be provided to support all the different elements and parts of the suction fixing device 10, and the joint element 22 allows a tilt between the frame 28 and the low pressure casing 12 and the attachment device 14. A holding device 20 also can be provided at a lower end of the frame 28. The holding device 20 can include a number of pins, spikes or the like, or a friction frame (e.g., a frame portion for contacting the bone structure, wherein the friction frame includes a ruff or abrasive surface), such that a lower end or ends of the holding device 20 are in the same plane as the attachment device or attachment lip 14. When atmospheric pressure presses the device 10 against the surface of a bone 50, the attachment device 14 is pressed with it, thus urging the tips of the pins of the holding device 20 against the surface of the bone 50. The pins of the holding device 20 can also be elongated or shortened. This can help the device 10 resist shifting or rotational forces, such that the device 10 is more secure.

The frame 28 also can be provided with one or more recesses. One of the recesses may be a recess 30, which can provide a lead-through or guide for the connection line 24 between the low-pressure casing or suction cup 12 and the valve or adapter means 16. The recess 30 can have larger dimensions and in particular a larger diameter than the diameter of the connection or flexible connection 24. This enables the joint element or joint 22 to rotate without being limited by the edges of the recess 30. The connection line 24, at least part of which can be flexible, can be threaded at its upper end. This threaded upper end 15 also can be used for biasing the device 10 with respect to the bone or joint structure. A fastening wheel 34 can be rotated for screwing the flexible connection towards the bone 50 or away from the bone 50.

When using the device 10, a soft tissue portal first is provided in order to access the surface of a patient's bone. The surgical field, for instance a hip or inlay, is then prepared for a computer-aided or image-guided operating techniques, wherein the device 10 is attached to the surface of the bone 50. A syringe 18, for example, then can be coupled to the adapter or valve means 16 and the syringe 18 (e.g., a piston of the syringe) is actuated to withdraw air or gas from the low-pressure casing 12 so as to generate a low-pressure atmosphere in the low-pressure casing 12. Once a low-pressure atmosphere has been generated, atmospheric pressure presses the device 10 against the surface of bone 50, thereby urging the holding device 20 (e.g., pins, spikes or ridges) against the surface of the bone 50. The reference or marker array 36 then can be adjusted to allow the computer-aided or image-guided operating technique to proceed. The valve or adapter means 16 can be fixed to the frame 28 or the joint element 22 by means of a fastening device or the fastening wheel 34, such that the whole valve or adapter means 16, the flexible connection 24 and the low-pressure casing 12 with the attachment device 14 can be exchanged quickly.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A suction fixing device configured to be fixed to an associated organic base, the suction fixing device comprising:
    a low-pressure casing configured to apply a low pressure to an associated surface of the associated organic base;
    an attachment device on the low-pressure casing, the attachment device defining a sealing surface configured to form a seal between the low-pressure casing and the associated surface of the associated organic base to selectively communicate the low pressure within the low-pressure casing to the associated surface of the associated organic base thereby securely holding the low-pressure casing to the associated organic base;
    a holding device configured to secure the fixing device with the associated organic base, the holding device comprising a bone engaging portion with friction enhancing projections separate from the attachment device, the friction enhancing projections being formed by at least one of a pin, a spike, or a friction frame including a roughened or abrasive surface, the friction enhancing projections having tips being configured to engage the associated surface of the associated organic base and selectively fix the holding device against lateral movement relative to the associated organic base upon application of the low pressure by the attachment device;
    at least one marker configured for use in computer-aided surgery, the at least one marker being coupled with the holding device;
    a first joint element coupled by a first side with a surface of the holding device, the first joint element being operable to provide selective relative rotational movement into a selected position between the holding device and a second side of the first joint element opposite to the first side of the first joint element; and
    a second joint element coupling the second side of the first joint element with the low-pressure casing, the second joint element being operable to provide selective relative translational movement into a selected locked position between the low pressure casing and the second side of the first joint element, the first and second joint elements and the holding device thereby providing for selective changing of a relative locked position between the attachment device and the friction enhancing projections, wherein the relative locked position is locked by the low pressure within the low-pressure casing being selectively communicated to the associated surface of the associated organic base.

2. The device of claim 1, wherein the friction enhancing projections are formed by a plurality of spikes.

3. The device according to claim 1, further comprising an evacuation device configured to generate the low pressure in the low-pressure casing.

4. The device according to claim 3, wherein the evacuation device is a syringe.

5. The device according to claim 3, further comprising a flexible connection interposed between the attachment device and at least one of the evacuation device or a valve of the evacuation device.

6. The device according to claim 3, wherein the evacuation device is integrated with the fixing device.

7. The device according to claim 1, wherein the friction enhancing projections of the holding device are configured to engage a bone or bone structure.

8. The device according to claim 1, further comprising at least one valve for connecting an evacuation device, said evacuation device configured to generate the low pressure in said low-pressure casing.

9. The device according to claim 1, wherein the first joint element is a ball joint and the second joint element is a threaded joint.

10. The device according to claim 1, wherein the surface of the holding device comprises a frame, said frame operatively supporting at least one of the low-pressure casing or the attachment device relative to the bone engaging portion of the holding device.

11. The device according to claim 10, wherein the first joint element is connected with said frame.

12. A suction fixing device configured to be fixed to an associated organic base, the suction fixing device comprising:
- a low-pressure casing configured to apply a low pressure to an associated surface of the associated organic base;
- an attachment device on the low-pressure casing, the attachment device being configured to communicate the low pressure from the low pressure casing to the associated surface of the associated organic base and form a seal between the low pressure casing and the associated surface of the associated organic base thereby securely holding the low-pressure casing to the associated organic base;
- a frame;
- a holding device connected with the frame and configured to secure the fixing device with the associated organic base, the holding device comprising a bone engaging portion with friction enhancing projections separate from the attachment device, the friction enhancing projections being formed by at least one of a pin, a spike, or a friction frame including a roughened or abrasive surface, the friction enhancing projections having tips configured to engage the associated surface of the associated organic base and selectively fix the holding device against lateral movement relative to the associated organic base upon application of the low pressure by the attachment device;
- at least one marker configured for use in computer-aided surgery, the at least one marker being coupled with the frame;
- a first joint element coupled by a first side with a surface of the frame, the first joint element being operable to provide selective relative rotational movement into a selected position between the frame and a second side of the first joint element opposite to the first side of the first joint element; and
- a second joint element coupling the second side of the first joint element with the low-pressure casing, the second joint element being operable to provide selective relative translational movement into a selected locked position between the low pressure casing and the second side of the first joint element, the first and second joint elements and the holding device thereby providing for selective changing of a relative locked position between the attachment device and the friction enhancing projections, wherein the relative locked position is locked by the low pressure within the low-pressure casing being selectively communicated to the associated surface of the associated organic base;
- wherein the frame comprises a recess enabling a portion of the low pressure casing and the attachment device carried thereon to pass into the recess and through the frame.

13. The device according to claim 12, wherein said recess is dimensioned so as to allow movements of the first joint element without interference.

14. The device of claim 1, wherein the friction enhancing projections are formed by a plurality of pins.

15. The device of claim 1, wherein the friction enhancing projections are formed by a plurality of roughened surfaces.

16. The device of claim 1, wherein the friction enhancing projections are formed by a plurality of abrasive surfaces.

17. A suction fixing device configured to be fixed to an associated organic base, the suction fixing device comprising:
- a low-pressure casing configured to selectively apply a low pressure to an associated surface of the associated organic base;
- an attachment device on the low-pressure casing, the attachment device being configured to communicate the low pressure from the low pressure casing to the associated surface of the associated organic base and form a seal between the low pressure casing and the associated surface of the associated organic base, thereby securely holding the low-pressure casing to the associated organic base;
- a holding device separate from the attachment device and configured to secure the fixing device to the associated organic base, the holding device comprising a bone engaging portion with friction enhancing projections separate from the attachment device, the friction enhancing projections being formed by at least one of a pin, a spike, or a friction frame including a roughened or abrasive surface, wherein the holding device selectively engages at a tip of the holding device the associated surface of the associated organic base when the low pressure is applied by the attachment device to the associated surface of the associated organic base;
- a valve configured for selective fluid connection between an associated evacuation device and the low pressure casing;
- a flexible connection operatively coupling the low-pressure casing with the valve;
- at least one marker configured for use in computer-aided surgery, the at least one marker being coupled with the holding device;
- a first joint element coupled by a first side with a surface of the holding device, the first joint element being operable to provide selective relative rotational movement into a selected position between the holding device and a second side of the first joint element opposite to the first side of the first joint element; and
- a second joint element coupling the second side of the first joint element with the low-pressure casing, the second joint element being operable to provide selective relative translational movement into a selected locked position between the low pressure casing and the second side of the first joint element, the first and second joint elements and the holding device thereby providing for selective changing of a relative locked position between the attachment device and the tip of the holding device, wherein the relative locked position is locked by the low pressure within the low-pressure casing being selectively communicated to the associated surface of the associated organic base.

18. The device of claim 17, wherein the flexible connection has a first end removably coupled with the low-pressure casing and a second end removably coupled with the valve.

19. The device according to claim 11, further comprising a coupling element that supports the at least one marker wherein the coupling element is coupled to the frame.

20. The device according to claim 1, wherein the at least one marker is trackable by a medical navigation system.

21. The suction fixing device according to claim 12, wherein:
- the first joint element is a ball joint; and
- the second joint element is a threaded joint.

22. The suction fixing device according to claim 17, wherein:
- the first joint element is a ball joint; and
- the second joint element is a threaded joint.

* * * * *